(12) United States Patent
Joshi et al.

(10) Patent No.: US 7,236,562 B2
(45) Date of Patent: Jun. 26, 2007

(54) METHOD OF ASSEMBLY AND THERMAL MANAGEMENT OF CT DETECTOR ELECTRONICS CIRCUITS

(75) Inventors: Ashutosh Joshi, Waukesha, WI (US); Joe James Lacey, Cambridge, WI (US); Mark A Kappel, Brookfield, WI (US); Mayank Gupta, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/163,905

(22) Filed: Nov. 3, 2005

(65) Prior Publication Data

US 2007/0098137 A1 May 3, 2007

(51) Int. Cl.
*A61B 6/00* (2006.01)
(52) U.S. Cl. .......................................... 378/19; 378/199
(58) Field of Classification Search .................. 378/19, 378/199
See application file for complete search history.

(56) References Cited

U.S. PATENT DOCUMENTS

| | | | | |
|---|---|---|---|---|
| 5,444,752 A | * | 8/1995 | Dobbs et al. ................. 378/19 |
| 5,596,228 A | * | 1/1997 | Anderton et al. ........... 257/714 |
| 6,249,563 B1 | * | 6/2001 | Snyder et al. ................ 378/19 |
| 6,582,616 B2 | * | 6/2003 | Kang et al. .................... 216/13 |
| 6,865,254 B2 | | 3/2005 | Nafstadius ..................... 378/65 |
| 6,967,126 B2 | * | 11/2005 | Lee et al. .................... 438/122 |
| 2002/0011097 A1 | * | 1/2002 | Kuderer et al. ............ 73/61.57 |
| 2004/0041257 A1 | * | 3/2004 | Tobita et al. ............... 257/720 |
| 2004/0051172 A1 | * | 3/2004 | Miyazaki et al. ........... 257/706 |
| 2004/0144723 A1 | * | 7/2004 | Gloeckle et al. ............ 210/640 |
| 2004/0184240 A1 | * | 9/2004 | Su ............... 361/717 |
| 2004/0202287 A1 | * | 10/2004 | Muller ....................... 378/199 |
| 2004/0228450 A1 | * | 11/2004 | Mueller ..................... 378/199 |
| 2004/0240625 A1 | * | 12/2004 | Kendall ..................... 378/199 |
| 2005/0139757 A1 | * | 6/2005 | Iwanczyk et al. ........... 250/239 |

* cited by examiner

*Primary Examiner*—Edward J. Glick
*Assistant Examiner*—Anastasia S. Midkiff
(74) *Attorney, Agent, or Firm*—Cantor Colburn LLP (57) ABSTRACT

Disclosed herein is a method for assembly of Computed Tomography (CT) Detector electronic circuits. A thermally conductive adhesive is dispensed on a first side of a first circuit board, the first circuit board having a plurality of ball grid arrays and a plurality of thermal sensors attached to the first side of the first circuit board. The thermally conductive adhesive is also dispensed on a first side of a second circuit board, the second circuit board having a plurality of ball grid arrays and a plurality of thermal sensors attached to the first side of the second circuit board. A first heat sink is mounted to the first side of the first circuit board. A second heat sink mounted to the first side of the second circuit board. The adhesive is cured on the first and the second circuit boards. The first circuit board is attached to the second circuit board, wherein the second side of the first circuit board is adjacent to the second side of the second circuit board.

14 Claims, 10 Drawing Sheets

METHOD OF ASSEMBLY AND THERMAL MANAGEMENT OF CT DETECTOR ELECTRONICS CIRCUITS

BACKGROUND OF THE INVENTION

This application relates generally to Computed Tomography (CT) systems. In particular, the invention relates to the method of assembly and thermal management of CT detector electronics. CT systems are used to obtain non-invasive sectional images of test objects, particularly internal images of human tissue for medical analysis and treatment. In a CT system, an x-ray source projects a fan-shaped beam that is collimated to lie within an X-Y plane of a Cartesian coordinate system, termed the "imaging plane." The x-ray beam passes through the object being imaged, such as a medical patient, and impinges upon a multi-row multi-column detector array. The detector array comprises a plurality of detector elements. The detector system converts incident X-rays of varying intensity into electronic signals. These analog signals are amplified and converted to digital pulses. CT system detector electronics use integrated circuit boards that process electronic the signals during CT system scans. Electronic signal conversion from analog to digital generates significant amounts of heat. Gantry air, primarily through forced air from axial fans, is used to cool the detector electronics, although gantry air can vary significantly. Newer generation CT systems have increasingly more electronic devices, and thus increased heat load that require further cooling. Existing CT systems do not have speed control fans or thermal management systems that provide reports on the thermal health of system components. Maintaining the thermal health of CT system components aids in preventing any degradation in CT system performance, which can cause image artifacts.

BRIEF SUMMARY OF THE INVENTION

Disclosed herein is a method for assembly of Computed Tomography (CT) Detector electronic circuits. A thermally conductive adhesive is dispensed on a first side of a first circuit board, the first circuit board having a plurality of ball grid arrays and a plurality of thermal sensors attached to the first side of the first circuit board. The thermally conductive adhesive is also dispensed on a first side of a second circuit board, the second circuit board having a plurality of ball grid arrays and a plurality of thermal sensors attached to the first side of the second circuit board. A first heat sink is mounted to the first side of the first circuit board. A second heat sink is mounted to the first side of the second circuit board. The adhesive is cured on the first and the second circuit boards. The first circuit board is attached to the second circuit board, wherein the second side of the first circuit board is adjacent to the second side of the second circuit board.

Further disclosed herein is a method for thermal management of a CT system. A CT system temperature is sensed. The CT system temperature is read as an input to a controller. The input is processed through an algorithm within the controller. The CT system temperature is regulated, based on the algorithm output, by controlling a variable speed fan. The mechanism degradation is reported within the CT system.

Yet further disclosed herein is a thermal management system for a CT system. The system having a variable speed fan, an Analog to Digital (A/D) assembly, a first and a second circuit board, a first and a second heat sink, a plurality of ball grid arrays, a plurality of thermal sensors, and a fan controller. The A/D assembly has a first and a second circuit board. The first and the second circuit board each have a heat sink and a plurality of ball grid arrays. A plurality of thermal sensors are installed on each of the first and the second circuit boards adjacent to the plurality of ball grid arrays and adhered to the heat sinks. The fan controller, which is configured to operate the fan, is responsive to the plurality of thermal sensors and the fan is responsive to the fan controller.

BRIEF DESCRIPTION OF THE DRAWINGS

Referring to the exemplary drawings wherein like elements are numbered alike in the accompanying Figures.

DETAILED DESCRIPTION OF THE INVENTION

Figure 1:
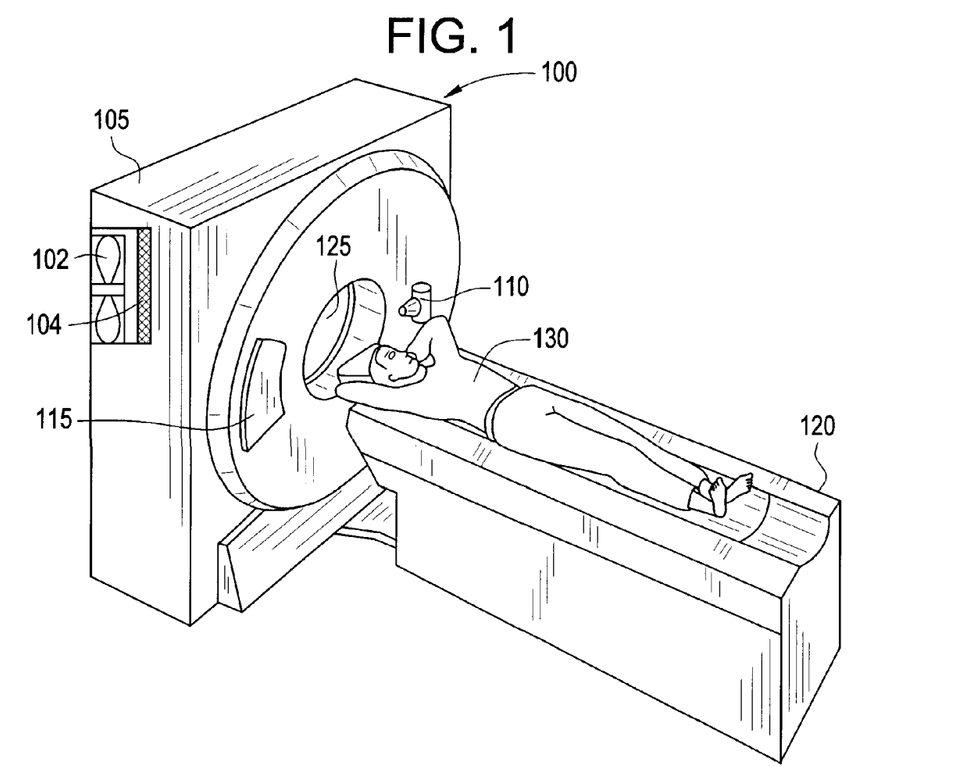
FIG. 1 is a perspective view of a CT imaging system and a patient disposed for imaging in accordance with an exemplary embodiment.
Figure 2:
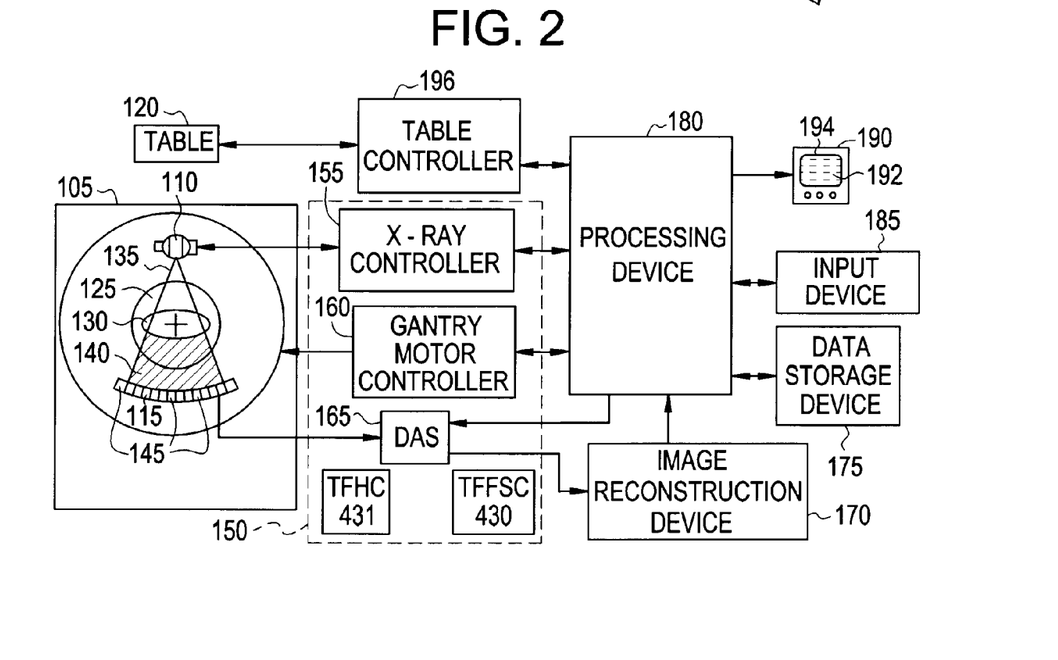
FIG. 2 is a block schematic diagram of a CT imaging system in accordance with an exemplary embodiment.

FIGS. 1 and 2 illustrate an exemplary CT imaging system 100 including a gantry 105 having an x-ray source 110, a radiation detector array 115, a patient support structure 120 and a patient cavity 125, wherein the x-ray source 110 and the radiation detector array 115 are opposingly disposed so as to be separated by the patient cavity 125. In an exemplary embodiment, a patient 130 is disposed upon the patient support structure 120, which is then disposed within the patient cavity 125. The x-ray source 110 projects an x-ray beam 135 toward the radiation detector array 115 so as to pass through the patient 130. In an exemplary embodiment, the x-ray beam 135 is collimated by a collimator (not shown) so as to lie within an X-Y plane of a Cartesian coordinate system referred to as an "imaging plane". After passing through and becoming attenuated by the patient 130, the attenuated x-ray beam 140 is received by the radiation detector array 115. In an exemplary embodiment, the radiation detector array 115 includes a plurality of detector elements 145 wherein each of said detector elements 145 receives an attenuated x-ray beam 140 and produces an electrical signal responsive to the intensity of the attenuated x-ray beam 140.

In addition, the x-ray source 110 and the radiation detector array 115 are rotatingly disposed relative to the gantry 105 and the patient support structure 120, so as to allow the x-ray source 110 and the radiation detector array 115 to rotate around the patient support structure 120 when the patient support structure 120 is disposed within the patient cavity 125. X-ray projection data is obtained by rotating the x-ray source 110 and the radiation detector array 115 around the patient 130 during a scan. The x-ray source 110 and the radiation detector array 115 communicate with a control mechanism 150 associated with the CT imaging system 100. The control mechanism 150 controls the rotation and operation of the x-ray source 110 and the radiation detector array 115.

In an exemplary embodiment, the control mechanism 150 includes an x-ray controller 155 communicating with an x-ray source 110, a gantry motor controller 160, and a data acquisition system (DAS) 165 communicating with a radiation detector array 115. The CT system further includes a fan 102, and air filter 104 downstream of the fan 102, to provide cooling to the controller and associated electronics. The x-ray controller 155 provides power and timing signals to the x-ray source 110, the gantry motor controller 160 controls the rotational speed and angular position of the x-ray source 110, and the radiation detector array 115 and the DAS 165 receive the electrical signal data produced by detector elements 145 and convert this data into digital signals for subsequent processing. In an exemplary embodiment, the CT imaging system 100 also includes an image reconstruction device 170, a data storage device 175 and a processing device 180, wherein the processing device 180 communicates with the image reconstruction device 170, the gantry motor controller 160, the x-ray controller 155, the data storage device 175, an input device 185 and an output device 190. The CT imaging system 100 can also include a table controller 196 in communication with the processing device 180 and the patient support structure 120, so as to control the position of the patient support structure 120 relative to the patient cavity 125.

In accordance with an exemplary embodiment, the patient 130 is disposed on the patient support structure 120, which is then positioned by an operator via the processing device 180 so as to be disposed within the patient cavity 125. The gantry motor controller 160 is operated via processing device 180 so as to cause the x-ray source 110 and the radiation detector array 115 to rotate relative to the patient 130. The x-ray controller 155 is operated via the processing device 180 so as to cause the x-ray source 110 to emit and project a collimated x-ray beam 135 toward the radiation detector array 115 and hence toward the patient 130. The x-ray beam 135 passes through the patient 130 so as to create an attenuated x-ray beam 140, which is received by the radiation detector array 115.

The detector elements 145 receive the attenuated x-ray beam 140, produce electrical signal data responsive to the intensity of the attenuated x-ray beam 140 and communicate this electrical signal data to the DAS 165. The DAS 165 then converts this electrical signal data to digital signals and communicates both the digital signals and the electrical signal data to the image reconstruction device 170, which performs high-speed image reconstruction. This information is then communicated to the processing device 180, which stores the image in the data storage device 175 and displays the digital signal as an image via output device 190. In accordance with an exemplary embodiment, the output device 190 includes a display screen 194 having a plurality of discrete pixel elements 192.

Figure 3:
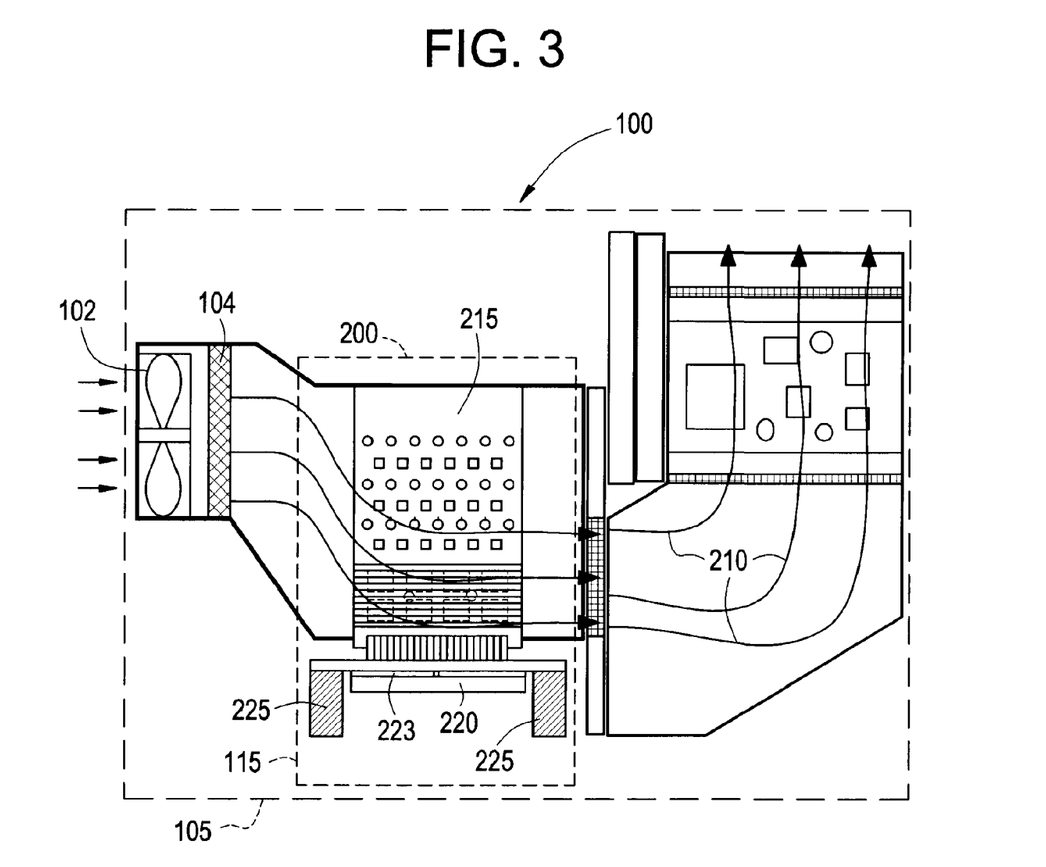
FIG. 3 is a partial section view of an exemplary gantry and exemplary detector array for use in accordance with an embodiment of the invention.

FIG. 3 further illustrates a partial section view of the gantry 105 and depicts an exemplary detector array 115, within the gantry 105, having a detector module 200 which includes an analog to digital (A/D) converter assembly 215, a collimator plate 220, a diode 223, and detector rails 225. Arrows and lines 210 originating from the fan 102 depict the flow path of cooling air through the CT system 100. The fan 102 speed can be varied as necessary to maintain the temperature of the CT system 100.

Figure 4:
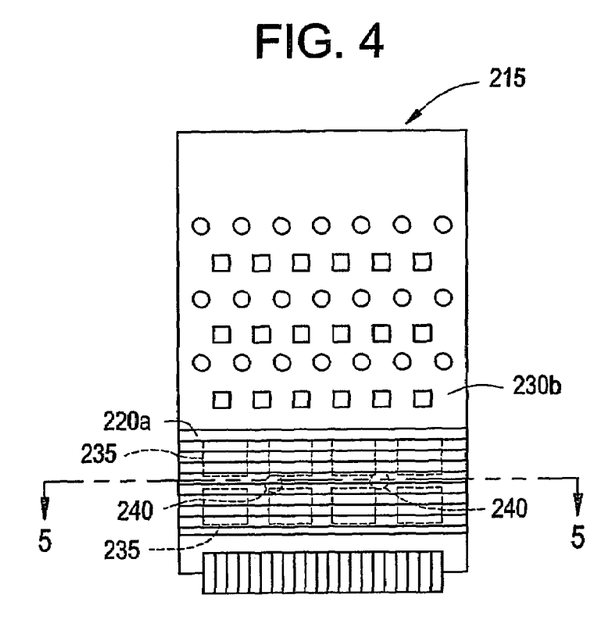
FIG. 4 is a top plan view of an exemplary A/D converter assembly for use in accordance with an embodiment of the invention.
Figure 5:
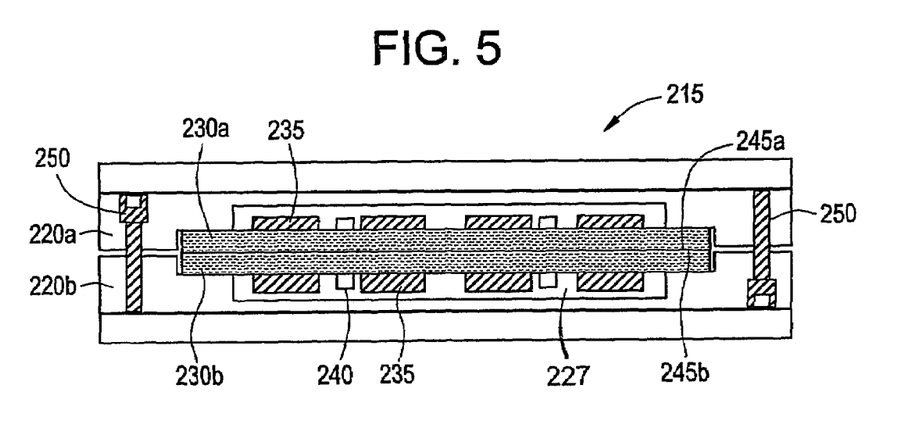
FIG. 5 is a cross section view of the exemplary A/D converter assembly of FIG. 4 for use in accordance with an embodiment of the invention.

FIG. 4 further illustrates an exemplary A/D converter assembly 215 having two heat sinks 220a and 220b (shown in FIG. 5), two one-sided circuit boards 230a and 230b (shown in FIG. 5), a plurality of ball grid arrays 235, and a plurality of thermal sensors 240. Each of the circuit boards 230a and 230b is constructed to have the thermal sensors 240 located within close proximity of the ball grid arrays 235, therefore allowing for accurate thermal measurements. Each circuit board 230a and 230b includes a plurality of thermal sensors 240 to monitor the temperature of the electronics and provide feedback so that fan 102 speed can be varied to maintain near constant temperature of the A/D converter assembly 215. Each of the circuit boards 230a and 230b is separately assembled including the mounting of the heat sinks 220a and 220b on each the circuit boards 230a and 230b. The heat sinks 220a and 220b are mounted on the circuit boards 230a and 230b by dispensing a very thin layer of highly thermally conductive silicone based adhesive, called potting material 227, over the multiple ball grid arrays 235 and the thermal sensors 240. The thermally conductive silicone based adhesive has an exemplary thermal conductivity of greater than or equal to 2 W/m-K but less than or equal to 3 W/m-K and an exemplary viscosity of less than 50,000 cpa. The heat sinks 220a and 220b are then placed on top of the potted circuit boards 230a and 230b in a fixture. The circuit boards 230a and 230b and heat sinks 220a and 220b assemblies are then cured, for about 1 to 2 hours at a temperature of greater than 100° C., to allow for the curing of the potting material. However, it will be appreciated that other curing procedures may be applied, such as UV curing for example. This method of mounting the heat sinks 220a and 220b to the circuit boards 230a and 230b results in a low thermal resistance between the ball grid arrays 235, the thermal sensors 240, and the heat sinks 220a and 220b. The method of assembly also reduces the stress on the circuit boards 230a and 230b and ball grid array solder joints, which are very sensitive to temperature cycling. After the individual circuit boards 230a and 230b are assembled and cured, the two circuit boards 230a and 230b are assembled together to make one A/D converter assembly 215. The two individual circuit boards 230a and 230b are assembled together, with the second sides 245a and 245b of the one-sided circuit boards 230a and 230b adjacent to each other as shown in the cross section view of FIG. 5. Fasteners 250 secured to the opposing heat sinks 220a and 220b hold the two circuit board/heat sink assemblies together to form one A/D converter assembly 215.

Figure 6:
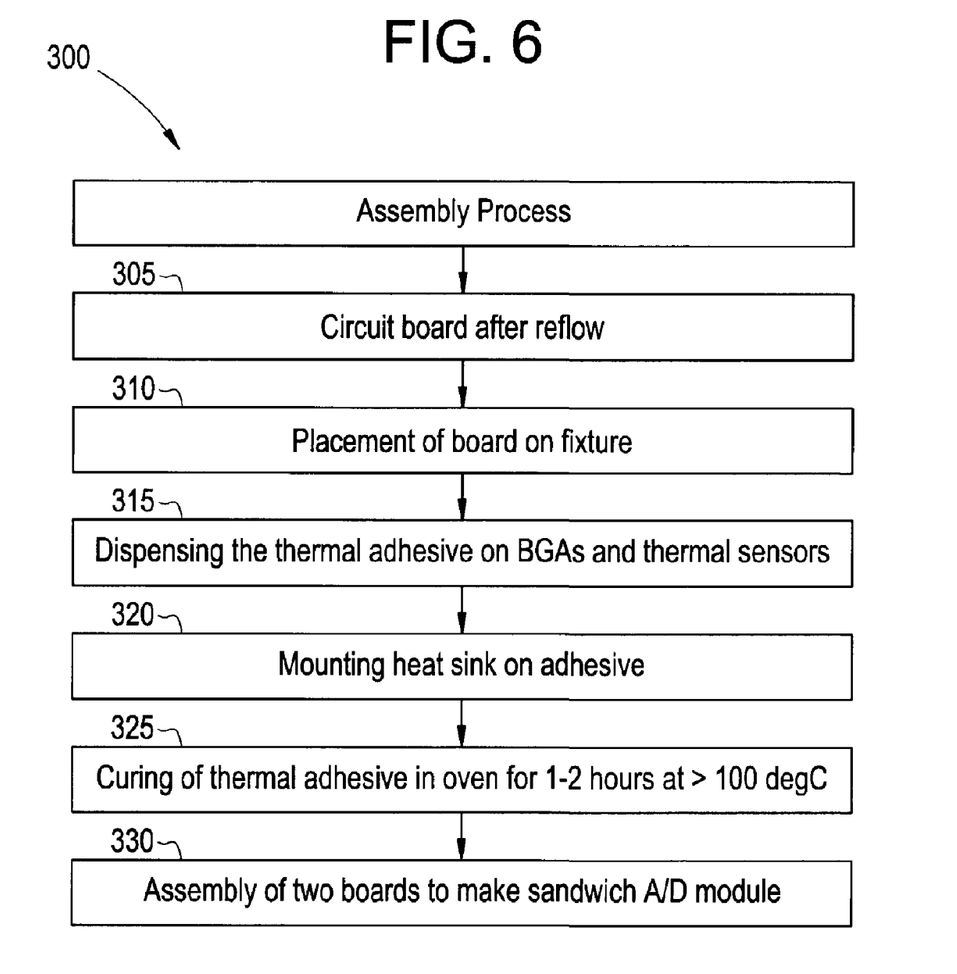
FIG. 6 is a flow chart of an exemplary process for assembly of the A/D converter assembly of FIG. 4 for use in accordance with the invention.

FIG. 6 illustrates an exemplary process for assembly 300 for the A/D converter assembly 215. The method of assembly begins with acquiring the circuit board 230a or 230b after reflow (step 305). Followed by placing the circuit board 230a or 230b on a fixture (step 310). Next, the thermal adhesive 227 is dispensed on the ball grid arrays 235 and thermal sensors 240 (step 315). Followed by mounting the heat sink 220a or 220b on the potted circuit board 230a or 230b (step 320). Next, curing of the thermal adhesive, in an oven for example, at the given approximate times and temperatures is performed (step 325). Lastly, the assembly of two circuit boards 230a or 230b with their respective heat sinks 220a and 220b are attached together to make on A/D converter assembly 215 (step 330).

Figure 7:
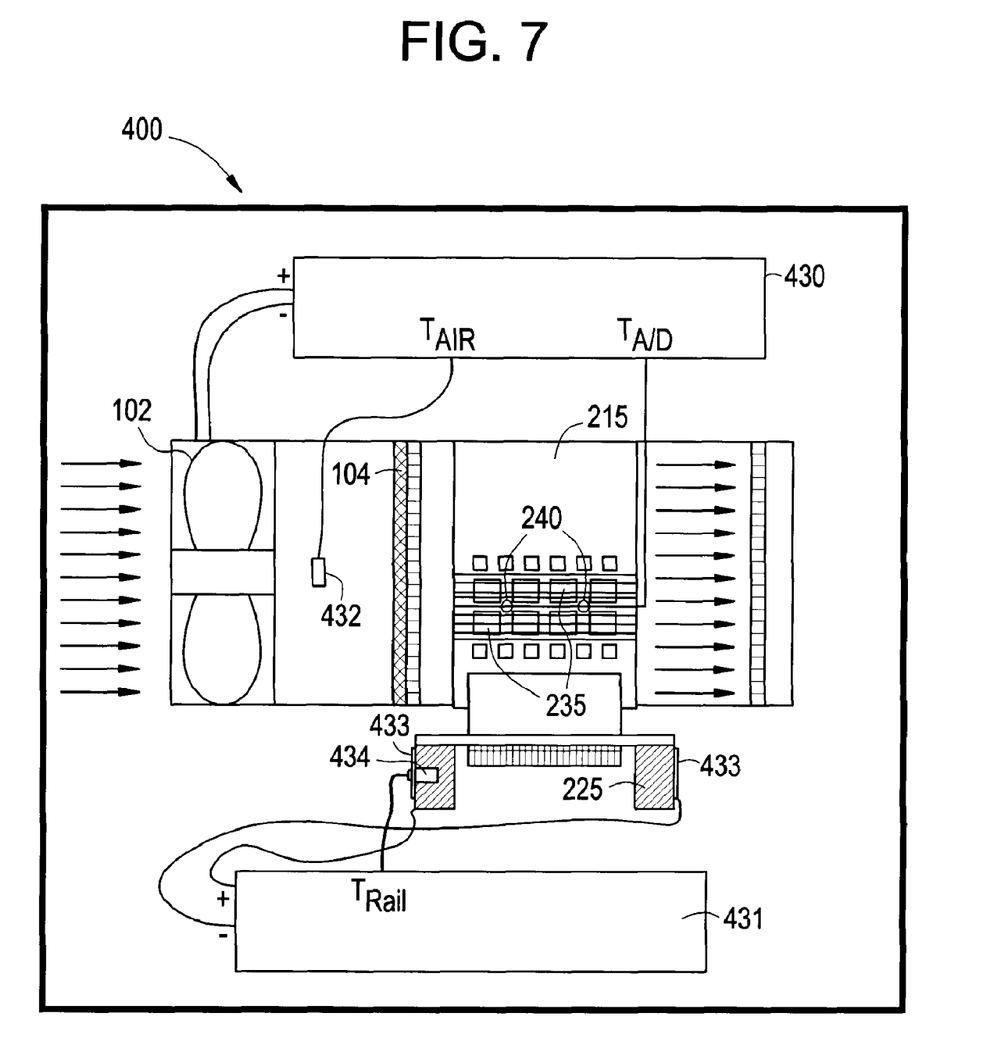
FIG. 7 is a system diagram of an exemplary temperature control system for use in accordance with an embodiment of the invention.

FIG. 7 illustrates a system diagram of an exemplary temperature control system 400. The temperature control system includes a Temperature Feedback Fan Speed Controller 430, which controls the fan 102 speed based on feedback from a plenum air temperature sensor 432, wherein the plenum air is part of the gantry air, and the A/D converter board thermal sensors 240. In an embodiment, the temperature control system may operate with a minimum of one plenum air temperature sensor 432 and one A/D converter board thermal sensor 240 for proper operation. In an alternative embodiment three plenum air temperature sensors 432 and twelve A/D converter board thermal sensors 240 may be used for redundancy in design. The temperature control system further includes a Temperature Feedback Heater Controller 431, which controls a three-zone rail heater 433, on the detector rails 225, based on rail temperature sensors 434. In an alternative embodiment, a rail heater system may include less than or more than three zones and the Temperature Feedback Fan Speed Controller 430 and the Temperature Feedback Heater Controller 431 may be within the control mechanism 150.

Figure 8:
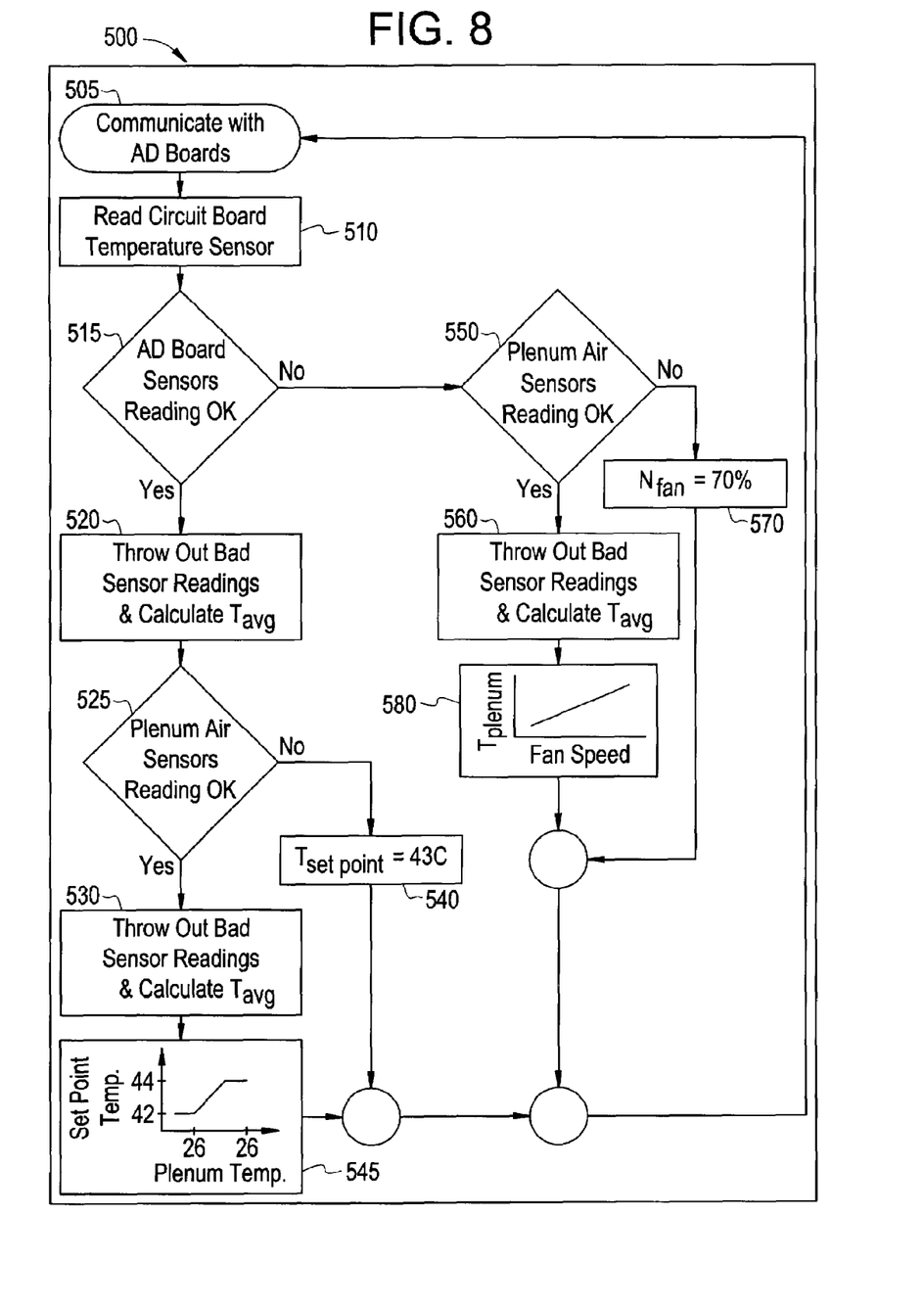
FIG. 8 is a block diagram of an exemplary detector plenum fan control algorithm for use in accordance with an embodiment of the invention.

FIG. 8 illustrates a block diagram of an exemplary detector plenum fan control algorithm 500, which is stored within the Temperature Feedback Fan Speed Controller 430. The Temperature Feedback Fan Speed Controller 430 first communicates with the circuit boards 230a and 230b (step 505) by receiving inputs from the A/D converter board thermal sensors 240 (step 510). If the circuit board(s) 230a and/or 230b temperature reading is acceptable (step 515), a new average temperature ($T_{avg}$) is calculated (step 520). Each CT detector array 115 has multiple detector modules 200 that consist of circuit boards 230a and 230b attached to the detector elements 145. In an embodiment, $T_{avg}$ is the average circuit board 230a and 230b temperature of three to five detector modules 200. Additionally, although it has been previously mentioned that three to five detector modules are used to calculate $T_{avg}$, it should be noted that quantities other than three to five, of detector modules, may be considered. Plenum Air temperature is next checked by receiving input from the plenum air temperature sensor 432. In an exemplary embodiment, the desired plenum air temperature is 30° C. and typically varies within +/−4° C. If the plenum air temperature is available, such that the sensor 432 is reading the plenum air temperature (step 525), then a new $T_{avg}$ is calculated (step 530) and a set point temperature ($T_{set\ point}$), which varies between 42° C. and 44° C., is assigned based on the plenum air temperature (step 545). $T_{set\ point}$ is defined by the average plenum temperature between 26° C. and 34° C. which is then varied linearly between 42° C. and 44° C. wherein average plenum temperatures below 26° C. are set to $T_{set\ point}$=42° C. and average plenum temperatures above 34° C. are set to $T_{set\ point}$=44° C. (step 545). If the plenum air temperature from step 525 is not available or acceptable, then $T_{set\ point}$ is fixed to 43° C. (step 540). If the A/D converter board thermal sensor 240 reading from step 515 is not available, due to a communication error for example, then the plenum air temperature is checked in step 550. If the plenum air temperature is available and acceptable, then a new $T_{avg}$ is calculated (step 560) and fan 102 speed is set by the plenum temperature (step 580). If the plenum air temperatures and A/D converter temperatures are not available in step 550, then fan 102 speed is set to a default of 70% of maximum fan 102 speed (step 570).

Figure 9:
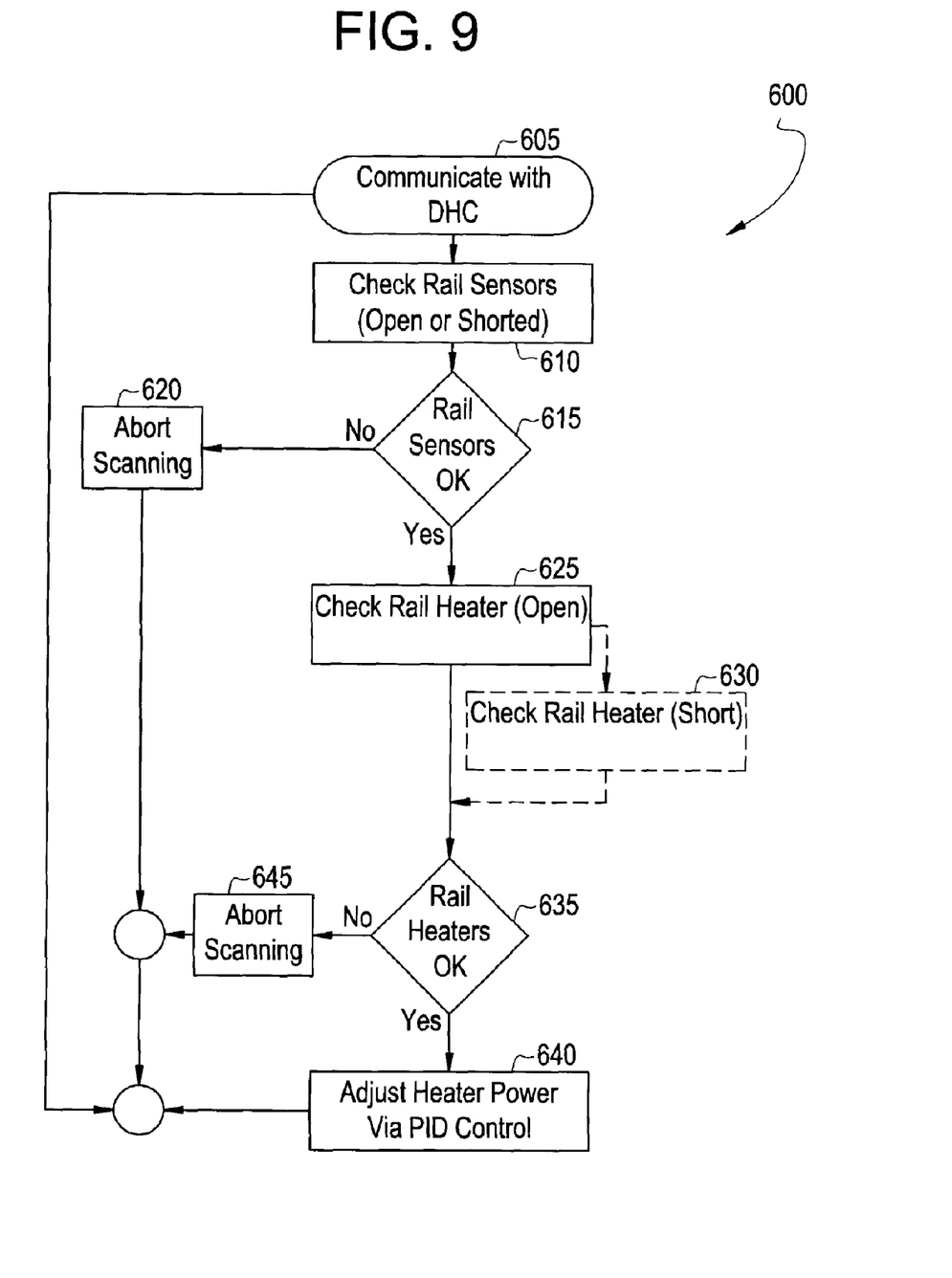
FIG. 9 is a block diagram of an exemplary detector rail heater control algorithm for use in accordance with an embodiment of the invention.

FIG. 9 illustrates a block diagram of an exemplary detector rail heater control algorithm 600, which is stored within the Temperature Feedback Heater Controller 431. The Temperature Feedback Heater Controller 431, or alternatively herein referred to as the Detector Heater Controller (DHC), first communicates with the rail temperature control sensors 434 (step 605) and checks the rail temperature control sensors 434 for an open or shorted condition (step 610). If the rail temperature control sensors 434 are not operating satisfactorily (step 615), then an abort scanning output signal is produced (step 620) and the next scan is inhibited. If the rail temperature control sensors 434 are operating satisfactorily (step 615), then the rail heaters 433 are checked for an open (step 625) or shorted (step 630) condition. Proper rail heater 433 operation (verified in step 635) results in adjusting heater power via PID (Proportional Integral Derivative) Control (step 640). If the rail heaters 433 are not operating properly (open or short detected) then an abort scanning output signal is yielded (step 645) resulting in subsequent scan inhibition.

Figure 10:
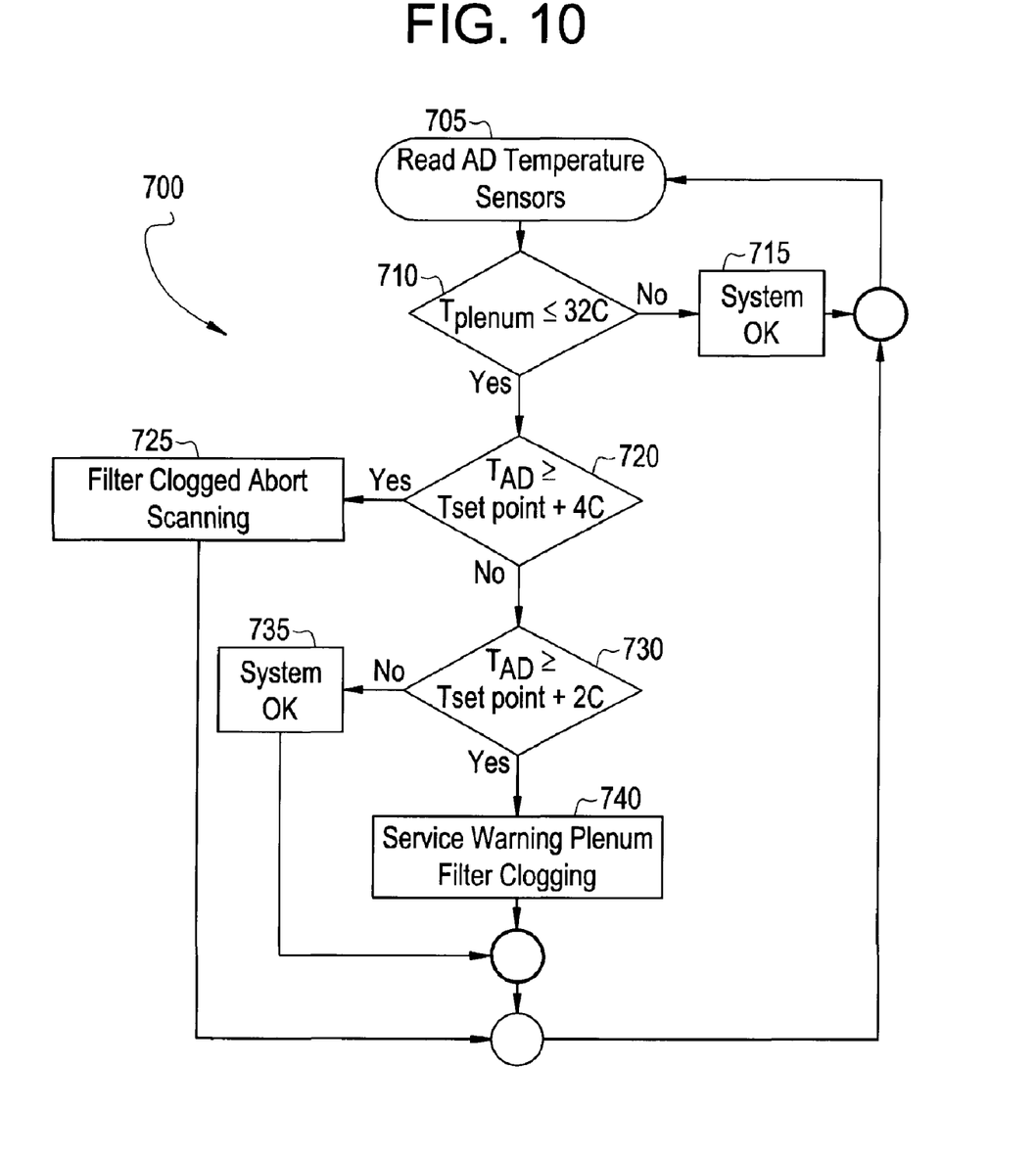
FIG. 10 is a block diagram of an exemplary filter health algorithm for use in accordance with an embodiment of the invention.
Figure 11:
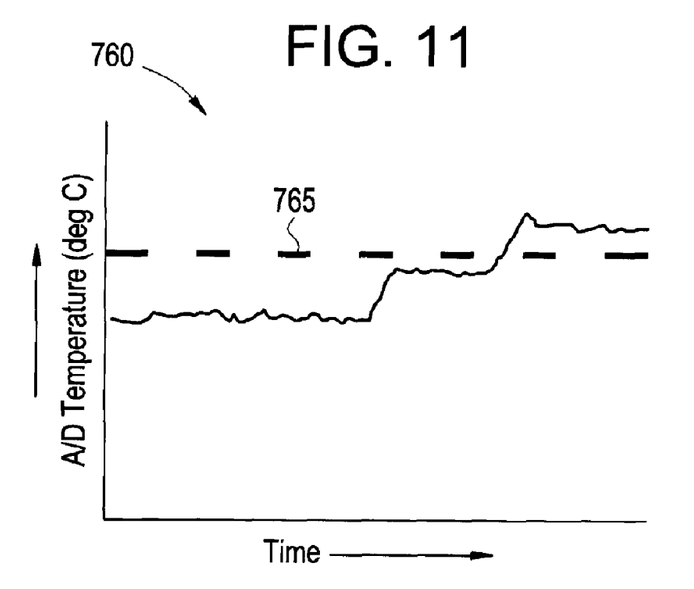
FIG. 11 is an exemplary graph of A/D temperature versus time for use in accordance with the invention.
Figure 12:
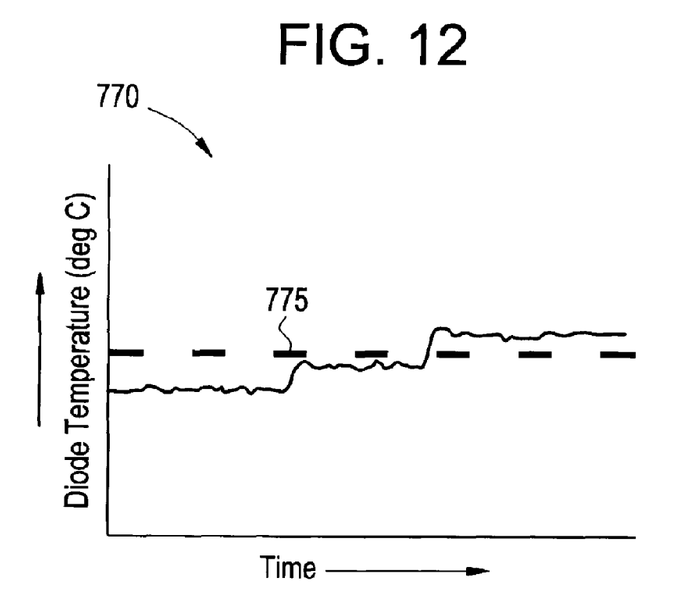
FIG. 12 is an exemplary graph of diode temperature versus time for use in accordance with the invention; and, FIG. 13 is an exemplary graph for the filter health algorithm for use in accordance with an embodiment of the invention.
Figure 13:
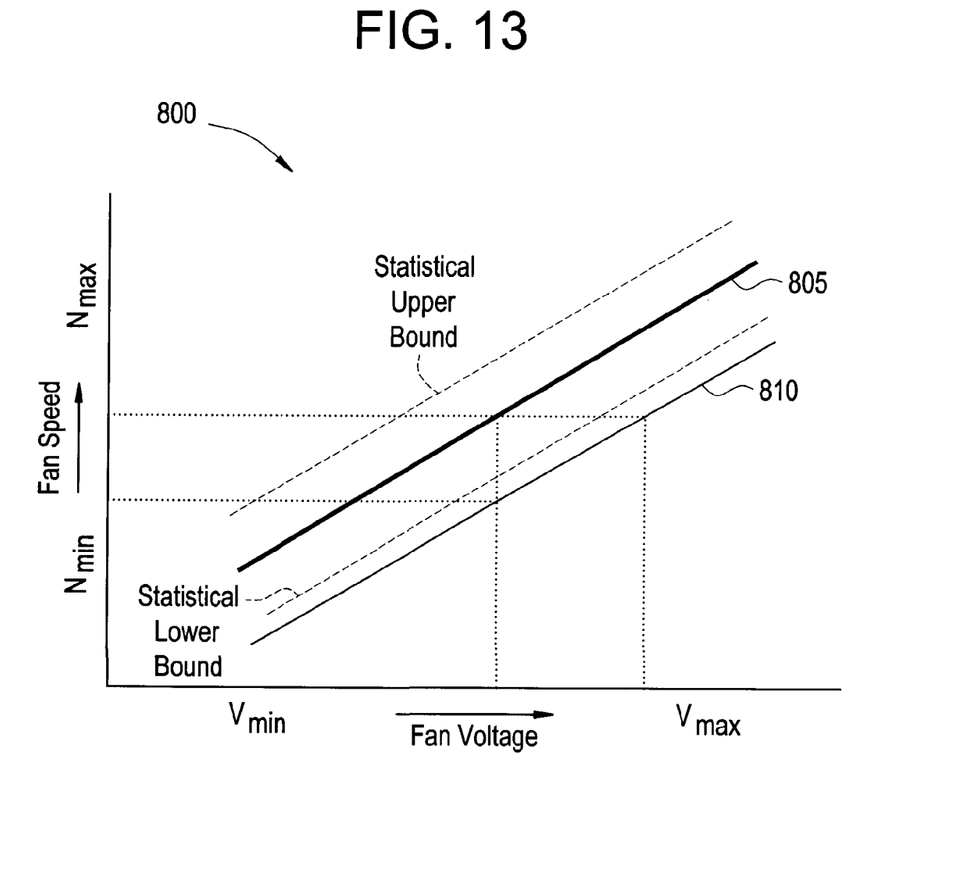

FIG. 10 illustrates a block diagram of an exemplary filter health algorithm 700. The prediction of a clogged air filter 104 is based on predicting the temperature rise of the A/D electronics for a certain inlet temperature. The filter health algorithm senses both A/D converter 215 circuit board temperatures ($T_{AD}$), from the A/D converter board thermal sensors 240, and plenum air temperature ($T_{plenum}$), from the plenum air temperature sensor 432. The algorithm first reads the A/D converter board 215 temperatures (step 705) and then checks whether or not plenum air temperature is less than or equal to 32° C. (step 710). If plenum air is greater than 32° C. then the system is operating normally (step 715). If plenum air is less than or equal to 32° C., then the A/D converter circuit board temperature is checked against a set point temperature ($T_{set\ point}$). If $T_{AD}$ is greater than or equal to $T_{set\ point}$+4° C. (step 720) then a "Filter Clogged, Abort Scanning" signal is sent to warn the operator and/or service personnel (step 725). If $T_{AD}$ is less than $T_{set\ point}$+4° C. (step 720), then A/D converter circuit board temperature is further compared against $T_{set\ point}$+2° C. (step 730). If $T_{AD}$ is less than $T_{set\ point}$+2° C., then the system is operating properly (step 735), on the other hand if $T_{AD}$ greater than or equal to $T_{set\ point}$+2° C., then a "Service Warning: Plenum Filter Clogging" indication warns the operator and/or service personnel (step 740). In an alternative embodiment, the filter health algorithm 700 further includes an A/D 215 Temperature versus time graph 760 and a Diode 223 Temperature versus time graph to predict a clogged air filter 104 illustrated in FIGS. 11 and 12. The A/D 215 Temperature graph 760 includes an A/D temperature corresponding to diode 223 temperature limit 765. The Diode 223 Temperature graph 770 includes a diode temperature limit 775. The limits 765 and 775 are used by the filter health algorithm 700 as predictive indictors corresponding to a potentially clogged air filter 104. In yet a further embodiment, the filter health algorithm 700 includes a Preemptive Fan Degradation algorithm 800, illustrated as a graph in FIG. 13. Fan 102 degradation may have similar indications to that of a clogged air filter 104. Therefore the filter health algorithm 700 may monitor fan 102 voltage and speed to determine whether indications result from a clogged air filter 104 or a degraded fan 102. Fan degradation is reported using a fan controller that reports instances when the prescribed fan speed doesn't match the corresponding fan voltage. A relationship between the fan 102 speed and the fan 102 voltage for a normally operating fan is illustrated in curve 805. A relationship between the fan 102 speed and the fan 102 voltage for a degraded fan is illustrated in curve 810. A degraded fan runs at a lower speed than a normal fan for the same voltage, or in other words, a degraded fan requires a higher voltage to match the normal fan speed. When a degraded fan condition is sensed, a warning is sent to the operator and/or service personnel.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A method for thermal management of a CT system comprising:
    sensing a CT system temperature at a circuit board having a plurality of thermal sensors adjacent a plurality of ball grid arrays;
    reading the CT system temperature as an input to a controller;
    processing the input through an algorithm within the controller;
    regulating the CT system temperature, based on an output of the algorithm, by controlling a variable speed fan; and,
    reporting a mechanism degradation within the CT system.

2. The method of claim 1 wherein the CT system further comprises a detector module having a circuit board and the regulating of the CT system temperature further comprises regulating the circuit board temperature.

3. The method of claim 1 wherein the sensing of the CT system temperature comprises sensing a plenum air temperature within the CT system.

4. The method of claim 3 wherein the controlling of the fan speed comprises controlling the fan speed in response to the plenum air temperature.

5. The method of claim 1 wherein the CT system further comprises a detector rail and the sensing of the CT system temperature comprises sensing a detector rail temperature.

6. The method of claim 5 wherein the CT system further comprises a detector rail heater attached to the detector rail and the regulating of CT system temperature comprises controlling the detector rail heater to maintain a CT system operating temperature.

7. A thermal management system for a CT system comprising:
    a variable speed fan;
    an Analog to Digital (A/D) assembly having a first and a second circuit board, the first and the second circuit board each having a heat sink and a plurality of ball grid arrays;
    a plurality of thermal sensors installed on each of the first and the second circuit boards adjacent to the plurality of ball grid arrays and adhered to the heat sinks; and,
    a fan controller, which is configured to operate the fan, wherein the fan controller is responsive to the plurality of thermal sensors and the fan is responsive to the fan controller.

8. The thermal management system of claim 7 further comprising a plenum air temperature sensor wherein the plenum air temperature sensor provides an input to the fan controller.

9. The thermal management system of claim 7 further comprising a detector rail in operable communication with the A/D assembly, the detector rail having a plurality of detector rail heaters and a plurality of detector rail temperature sensors in thermal communication with the detector rail.

10. The thermal management system of claim 9 further comprising a heater controller wherein the heater controller is configured to operate the plurality of detector rail heaters responsive to the plurality of detector rail temperature sensors.

11. The thermal management system of claim 7 wherein the fan controller comprises a control algorithm, and further comprises an air filter, wherein the control algorithm is configured to predict clogging of the filter.

12. The thermal management system of claim 11 wherein the fan controller is configured to display a service warning message when the algorithm is responsive to a clogged filter condition.

13. The thermal management system of claim 7 wherein an adhesive adhering the plurality of ball grid arrays to the heat sinks is a silicone based adhesive having a thermal conductivity greater than or equal to 2 W/m-K but less than or equal to 3 W/m-K.

14. The thermal management system of claim 7 wherein an adhesive adhering the plurality of ball grid arrays to the heat sinks is a silicone based adhesive having a viscosity less than 50,000 cpa.

* * * * *